(12) United States Patent
Yamauchi et al.

(10) Patent No.: US 6,707,289 B2
(45) Date of Patent: Mar. 16, 2004

(54) METHOD AND APPARATUS FOR AUTOMATIC REGISTRATION FOR A BOARD

(75) Inventors: Satoshi Yamauchi, Yamanashi (JP); Toshihiko Tsujikawa, Yamanashi (JP); Masayuki Kajiyama, Toyonaka (JP); Suehiro Tanaka, Yamanashi (JP)

(73) Assignee: Matsushita Electric Industrial Co., Ltd. (JP)

( * ) Notice: Subject to any disclaimer, the term of this patent is extended or adjusted under 35 U.S.C. 154(b) by 16 days.

(21) Appl. No.: 10/310,779

(22) Filed: Dec. 6, 2002

(65) Prior Publication Data

US 2003/0080727 A1 May 1, 2003

Related U.S. Application Data

(62) Division of application No. 09/696,176, filed on Oct. 26, 2000, now Pat. No. 6,512,363.

(30) Foreign Application Priority Data

Oct. 26, 1999 (JP) .................................. 11-303210

(51) Int. Cl.[7] .............................................. G01R 15/12
(52) U.S. Cl. ..................... 324/158.1; 324/758; 324/324; 324/761

(58) Field of Search ........................ 324/158.1, 758, 324/761, 73.1; 356/400, 401; 382/145; 348/87, 129, 95

(56) References Cited

U.S. PATENT DOCUMENTS

| 4,668,982 A | | 5/1987 | Tinnerino ..................... 348/87 |
| 4,783,826 A | | 11/1988 | Koso ............................. 382/8 |
| 4,820,975 A | | 4/1989 | Diggle ........................ 356/400 |
| 5,321,352 A | | 6/1994 | Takebuchi ................... 324/690 |
| 5,408,189 A | * | 4/1995 | Swart et al. ................. 324/758 |
| 5,422,575 A | * | 6/1995 | Ferrer et al. ................. 324/754 |
| 6,212,751 B1 | | 4/2001 | Hattori ....................... 324/758 |

FOREIGN PATENT DOCUMENTS

| GB | 2 327 302 | 1/1999 |
| JP | 06252596 | 9/1994 |
| WO | 99/41621 | 8/1999 |

* cited by examiner

Primary Examiner—Vinh P. Nguyen
(74) Attorney, Agent, or Firm—Parkhurst & Wendel, L.L.P.

(57) ABSTRACT

A high-precision inspection apparatus and method for inspecting a large board with a line sensor camera, the coordinate positions of correction marks on a pair of holding members are read by the camera and compared with predetermined coordinates, and an amount of positional discrepancy of the board is computed. The board is adjusted according to the positional discrepancy, if necessary, and then scanned.

3 Claims, 10 Drawing Sheets

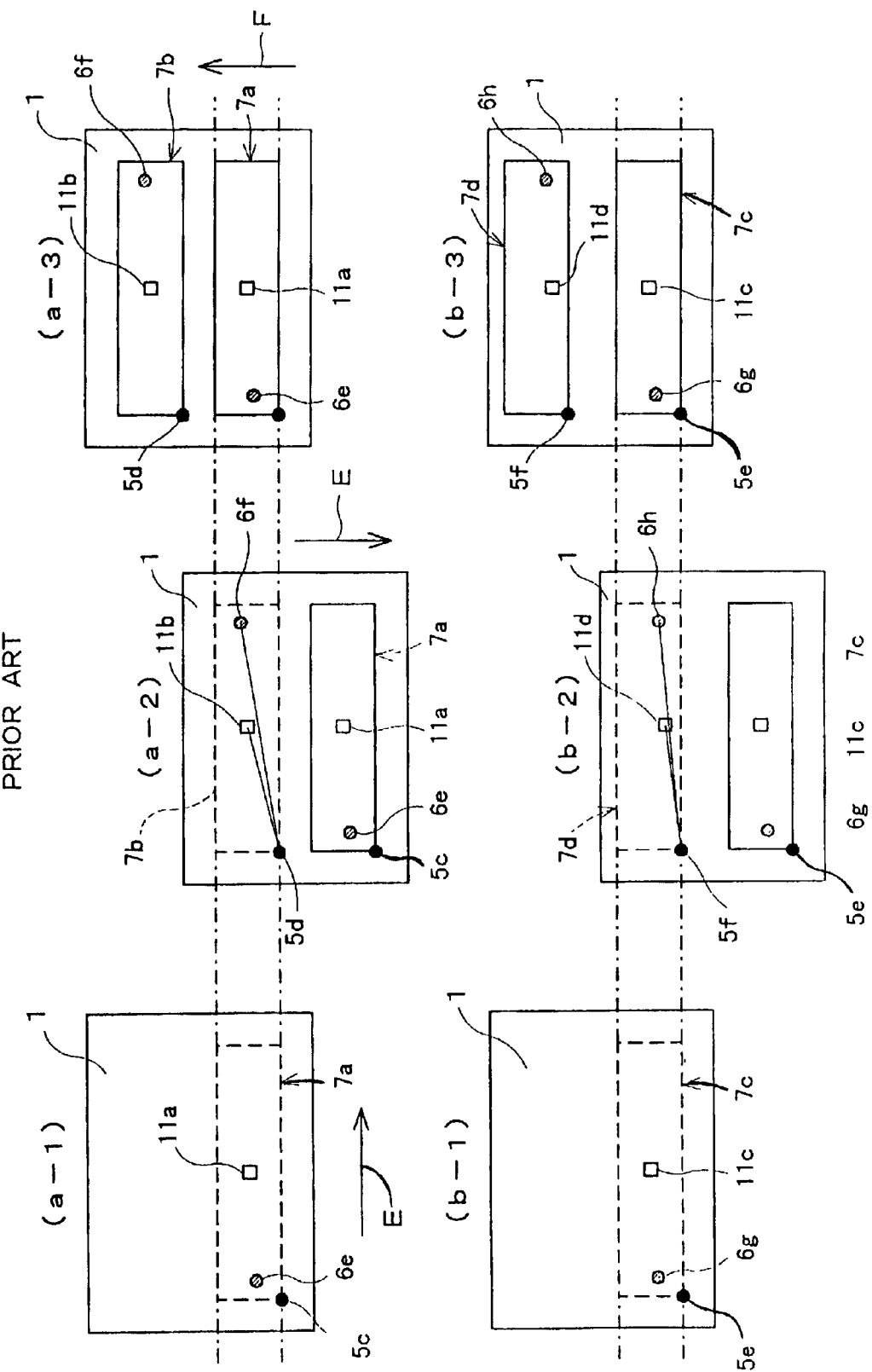

METHOD AND APPARATUS FOR AUTOMATIC REGISTRATION FOR A BOARD

This application is a divisional application of Ser. No. 09/696,176 filed Oct. 26, 2000, now U.S. Pat. No. 6,512,363 now allowed.

FIELD OF THE INVENTION

This invention relates to an inspection method and inspection apparatus wherein a board that has been conveyed to the inspection position is photographed with a line sensor camera and inspected.

BACKGROUND OF THE INVENTION

When electronic components are mounted to printed circuit boards, various kinds of inspections are performed. These include inspections of print conditions after solder printing, inspections of mounting conditions of mounted components, and inspections of conditions of components and solder after the solder has hardened.

One method for performing such inspections is the method of inspecting by using a line sensor camera to photograph boards that have been conveyed to an inspection position.

A conventional inspection apparatus is shown in FIGS. 7 to 10.

As shown in FIGS. 7 and 8, the inspection apparatus is configured such that an inspection is made by causing a line sensor camera 3 to photograph a printed circuit board 1 conveyed to an inspection position, by scanning that printed circuit board 1 in a direction (direction indicated by arrow C) along the direction of board conveyance.

More specifically, the printed circuit board 1 in the inspection position is held by a pair of rails 2 being constant in breadth and constituting a pair of holding members. The line sensor camera 3 is movable in the direction of arrow C by a movement shaft 8, and photographs the surface of the printed circuit board 1 through a reflecting mirror 10.

In an inspection apparatus configured in this way, the movement shaft 8 is sometimes caused to expand and contract or the printed circuit board 1 to expand and contract due to factors such as heat.

For this reason, in the printed circuit board 1 being inspected, as shown in FIG. 9, a first correction mark 6e and a second correction mark 6f are provided on the side where the line sensor camera 3 starts reading and on the side where it ends reading, respectively, such that these correction marks 6e and 6f are positioned on a diagonal line passing through the board 1. Using the correction marks in these two places, any discrepancy in the movement shaft 8 or printed circuit board 1 described above is corrected.

In more specific terms, when the printed circuit board 1 is photographed by the line sensor camera 3, the correction marks 6e and 6f are first recognized with the line sensor camera 3 and center positions therefor are found respectively. Coordinate positions for the correction marks 6e and 6f thus obtained by the recognition with the line sensor camera 3 are defined as $(x_e, y_e)$ and $(x_f, y_f)$ respectively.

Here, coordinate positions for the first and second correction marks 6e and 6f have been pre-taught as $(X_e, Y_e)$ and $(X_f, Y_f)$, respectively, and distances between the first correction mark 6e and the second correction mark 6f in the X axis direction and the Y axis direction have been known, so that based on the distances and the recognition with the line sensor camera, the ratios of the distances between the first and second correction marks 6e and 6f in the X axis direction and the Y axis direction are found, respectively, as $\gamma_x$ and $\gamma_y$, that may be expressed as;

$\gamma_x = |x_e - x_f| / |X_e - X_f|$ and $\gamma_y = |y_e - y_f| / |Y_e - Y_f|$.

When the ratios in the X axis direction and the Y axis direction are both valued 1, it can be judged that there is no expansion or contraction in the movement shaft 8 or the printed circuit board 1. When the ratio is other than 1, however, it is judged that there is expansion or contraction in the movement shaft 8 and/or printed circuit board 1, whereupon adjustments are made to respective coordinate positions in an image so that the recognized positions of the correction marks become the taught values, and the position of the printed circuit board 1 is also adjusted.

More specifically, assuming that the expansion and contraction are uniform, respective X-coordinate and Y-coordinate values in the recognized image are divided by $\gamma_x$ and $\gamma_y$ to produce corrected values so that a corrected image can be presented.

However, as will be explained below, there is a problem with the inspection method described in the foregoing in that it cannot be used when the printed circuit board 1 is so large in the breadth direction of the rails 2 that it cannot be thoroughly scanned by the line censor camera.

When the printed circuit board 1 is too large as mentioned above, one possibility is to provide the printed circuit board 1 with a screw shaft that is movable in the breadth direction of the rails 2. By rotating the screw shaft, the printed circuit board 1 is moved in the breadth direction of the rails 2a while photographs are taken with the line sensor camera 3 a plural number of times.

When the printed circuit board 1 is photographed two times with the line sensor camera 3, for example, first, as shown in FIG. 10(a-1), the line sensor camera 3 is moved from a first scan start position 5c in the direction indicated by arrow E1, whereupon a first scan area 7a wherein a first inspection point 11a is provided is photographed.

Next, as shown in FIG. 10(a-2), the printed circuit board 1 is moved in the direction indicated by arrow E2 by the screw shaft, and a second scan area 7b wherein a second inspection point 11b is provided is photographed from a second scan start position 5d.

The printed circuit board 1, after photographing is concluded, is moved in the direction indicated by arrow F by the screw shaft, as shown in FIG. 10(a-3), and returned to the original position.

When there is contained a process step for moving the printed circuit board 1 by a screw shaft in the breadth direction of the rails 2, as described above, there is a problem in that when printed circuit boards 1 are conveyed successively and each printed circuit board undergoes inspection, even if the position of the printed circuit board 1 is altered by rotating the screw shaft for the same amount each time, the resulting amount of movement will not be constant in actual practice because of the influence of the thermal expansion of the screw shaft.

FIGS. 10(b-1) to 10(b-3) show the inspection method for a case where there has been thermal expansion in the screw shaft.

FIG. 10(b-1), where photographing is done in the same manner as shown in FIG. 10(a-1), shows a reference position for moving the printed circuit board 1 with the screw shaft, so that the first scan start position 5c and the first scan start position 5e are at the same position, and there is no discrepancy between the first scan area 7a and the first scan area 7c photographed by the line sensor camera 3.

However, when thermal expansion occurs in the screw shaft, the moved printed circuit board 1, as shown in FIG. 10(b-2), even though the screw shaft is rotated for the same amount as shown in FIG. 10(a-2), exhibits a discrepancy between the second scan start position 5f and the second scan start position 5d in the breadth direction of the rails 2.

As a result, the distance from the second scan start position 5d to the second correction mark 6f as shown in FIG. 10(a-2) differs from the distance from the second scan start position 5f to the second correction mark 6h as shown in FIG. 10(b-2). Likewise, the distance from the second scan start position 5d to the second inspection point 11b as shown in FIG. 10(a-2) differs from the distance from the second scan start position 5f to the second inspection point 11d as shown in FIG. 10(b-2). Accordingly, overall dislocation has occurred between the image including the first scan area 7c and the second scan area 7d as shown in FIG. 10(b-3), and the image including the first scan area 7s and the second scan area 7b as shown in FIG. 10(a-3).

Thus, when a discrepancy in the rotational driving amount of the screw shaft occurs due to heat or the like, a discrepancy occurs in the scan start position, so that a contraction correction method that uses a first correction mark 6c and a second correction mark 6f, as described in the foregoing, cannot be employed.

SUMMARY OF THE INVENTION

An object of the present invention is to provide a high-precision inspection apparatus and inspection method capable of inspecting a large board by laterally moving the board and photographing the board for a plural number of times before and after the lateral moving.

The inspection method of the present invention is characterized in that a to-be-inspected board is moved laterally and an amount of movement of holding members of the board is corrected based on an amount of positional discrepancy of the board.

According to this aspect of the invention, large boards can be inspected, and high-precision inspections can be effected.

The inspection apparatus of the invention is characterized in that correction marks are provided on the holding members for holding the board.

According to this aspect of the invention, the inspection method of the present invention can be easily implemented.

The inspection method described in a first aspect of the present invention is a method for inspecting a to-be-inspected board by photographing the board that has been conveyed to an inspection position, in which a pair of holding members constituted of a pair of rails for holding the board are moved to move the board in a direction crossing a scanning direction of a linear sensor camera and the board that has been positioned is scanned by the photography unit along the direction of said conveyance of the board, the inspection method comprising: reading coordinate positions of correction marks applied to said holding members by said camera; computing an amount of positional discrepancy of the board by comparing coordinate positions of correction marks previously set with the coordinate position of correction marks having been read; and when there are discrepancies between said two kinds of coordinate positions, carrying out said photographing after correcting an amount of movement of the holding members based on said amount of positional discrepancy of the board.

The inspection method according to a second aspect of the present invention is a method for inspecting a to-be-inspected board by photographing the board that has been conveyed to an inspection position, in which a pair of holding members constituted of a pair of rails located in an opposed relation to each other for holding the board are moved to move the board in a direction crossing a scanning direction of a linear sensor camera and the board that has been positioned is scanned by the photography unit along the direction of said conveyance of the board, the inspection method comprising: reading a coordinate position of a first correction mark applied to one of the holding members by said camera; moving said holding members and reading a coordinate position of a second correction mark applied to the other of the holding members, said second correction mark on said the other of the holding members being on the side opposite to that of the first correction mark on said one of the holding members with the board being interposed therebetween; computing an amount of positional discrepancy of the board by comparing coordinate positions of first and second correction marks previously set with the coordinate positions of the first and second correction marks having been read; and when there are discrepancies between said two kinds of coordinate positions, carrying out said photographing after correcting an amount of movement of the holding members based on said amount of positional discrepancy of the board, wherein the first and second correction marks are provided on the side where the linear sensor camera starts reading.

The inspection method described in a third aspect of the present invention is a method for inspecting a to-be-inspected board by photographing the board that has been conveyed to an inspection position, in which a pair of holding members constituted of a pair of rails for holding the board are moved to move the board in a direction crossing a scanning direction of a linear sensor camera and the board that has been positioned is scanned by the photography unit along the direction of said conveyance of the board, the inspection method comprising: reading coordinate positions of correction mark applied to said board by said camera; computing an amount of positional discrepancy of said board by comparing coordinate positions of correction marks previously act with the coordinate positions of the correction marks having been read; and when there are discrepancies between said two kinds of coordinate positions, carrying out said photographing after correcting an amount of movement of the holding members based on said amount of positional discrepancy of the board, wherein first and second correction marks are provided on the side where the linear sensor camera starts reading, said second correction mark being provided on a diagonal line passing said first correction mark.

The inspection apparatus described in a fourth aspect of the present invention is an apparatus for inspecting a to-be-inspected board by photographing the board that has been conveyed to an inspection position, in which a pair of holding members constituted of a pair of rails for holding the board are moved to move the board in a direction crossing a scanning direction of a linear sensor camera and the board that has been positioned is scanned by the camera along the direction of said conveyance of the board, the inspection apparatus comprising: a control unit configured to read coordinate positions of correction marks applied to the holding members by the photography unit, to compute an amount of positional discrepancy of the board by comparing coordinate positions of correction marks previously set with the coordinate positions of the correction marks having been read, and when there are discrepancies between said two kinds of coordinate positions, to carry out said photographing after correcting an amount of movement of the holding members based on said amount of positional discrepancy of the board.

The inspection apparatus described in a fifth aspect of the present invention is an apparatus for inspecting a to-be-inspected board by photographing the board that has been conveyed to an inspection position, in which a pair of holding members constituted of a pair of rails for holding the board are moved to move the board in a direction crossing a scanning direction of a linear sensor camera and the board that has been positioned is scanned by the camera along the direction of said conveyance of the board, the inspection apparatus comprising: a control unit configured to read coordinate positions of correction marks applied to said board by the photography unit, to compute an amount of positional discrepancy of the board by comparing coordinate positions of correction marks previously set with the coordinate positions of the correction marks having been read, and when there are discrepancies between said two kinds of coordinate positions, to carry out the photographing after correcting an amount of movement of the holding members based on said amount of positional discrepancy of the board.

BRIEF DESCRIPTION OF THE DRAWINGS

FIG. 10 is a schematic illustration showing steps in a conventional inspection method.

DESCRIPTION OF THE PREFERRED EMBODIMENTS

Embodiment aspects are now described with the use of FIGS. 1 to 5.

In this description, the same or similar items as those indicated in FIGS. 7 to 10 diagramming the conventional example, as noted earlier, are designated by the same symbols.

First Embodiment

First embodiment in the present invention is shown in FIGS. 1 to 4.

Figure 1:
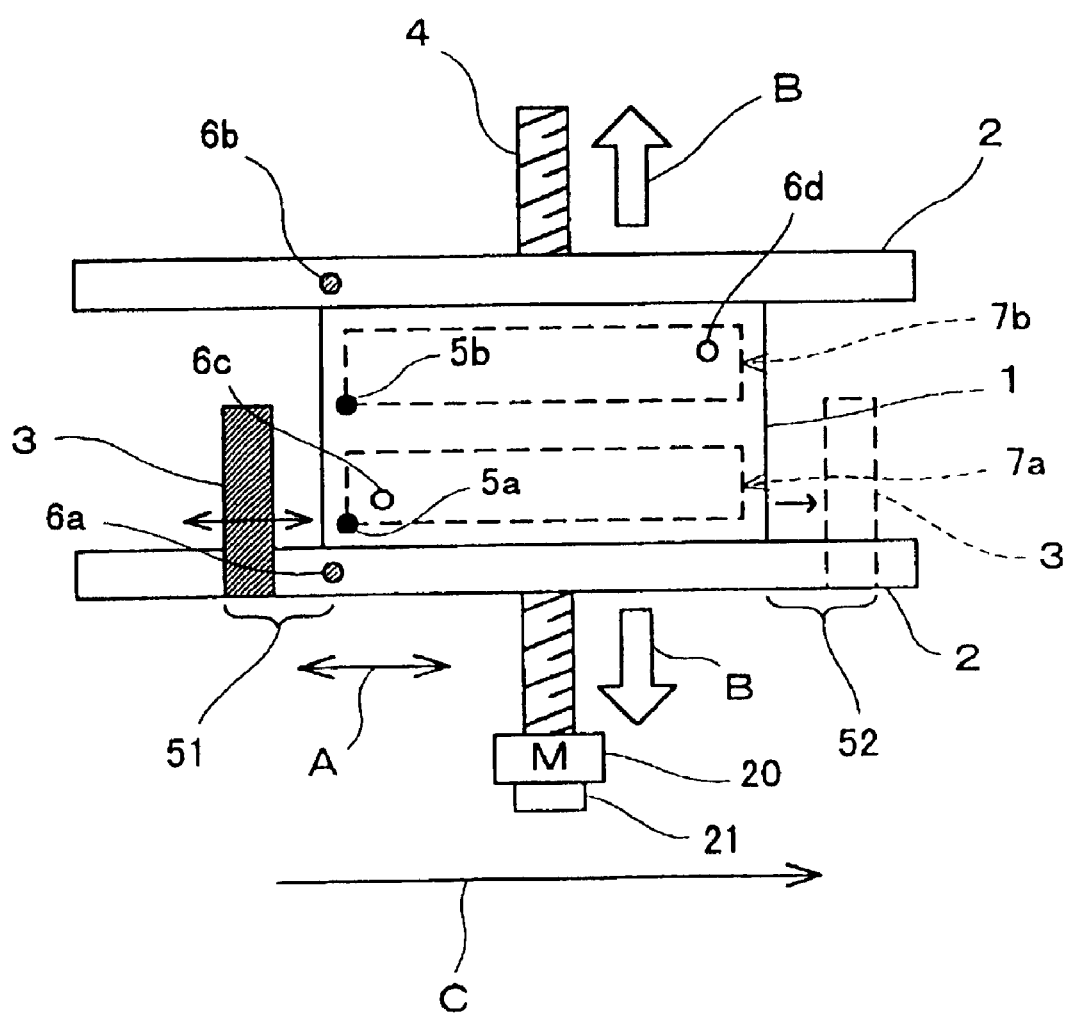
FIG. 1 is a schematic plan view of an inspection apparatus in a first embodiment of the present invention.

This first embodiment, as shown in FIG. 1, differs from the conventional example described earlier in that a screw shaft (ball screw shaft) 4 is provided for moving a printed circuit board 1, that is a board being inspected, in a direction crossing the direction of conveyance of the board (the direction indicated by arrow C), for example, in the breadth direction of a pair of rails 2 indicated by arrow B, and correction marks for correcting the amount of rotational drive of the screw shaft 4 are provided on the side of the rails 2.

Figure 2A:
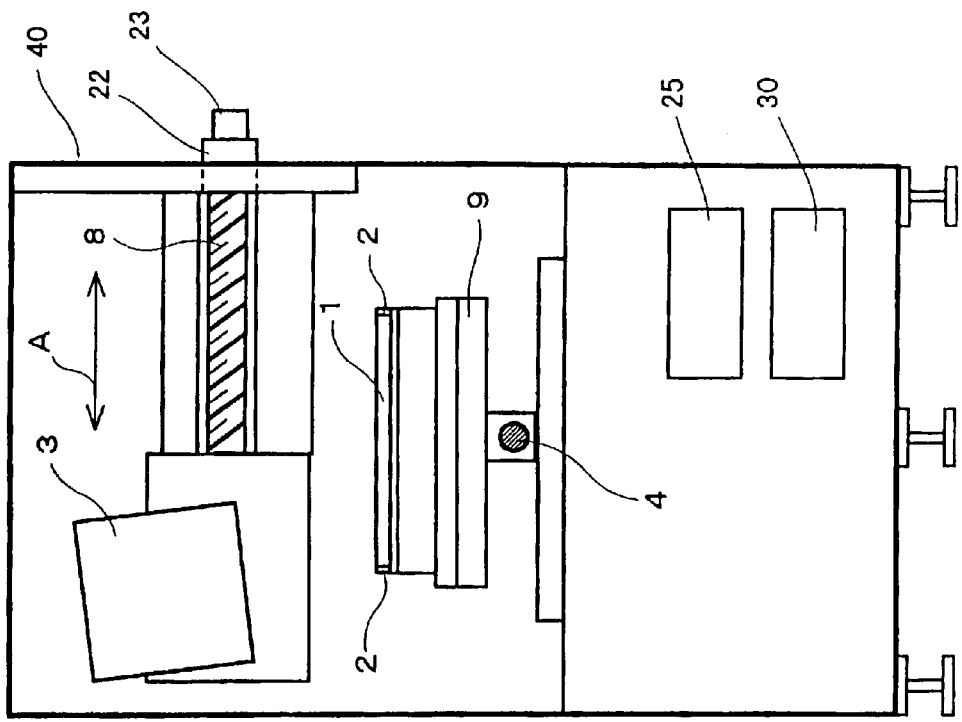
FIGS. 2(a)–2(b) are a side elevation and front elevation of the inspection apparatus in the first embodiment of the present invention.
Figure 2B:
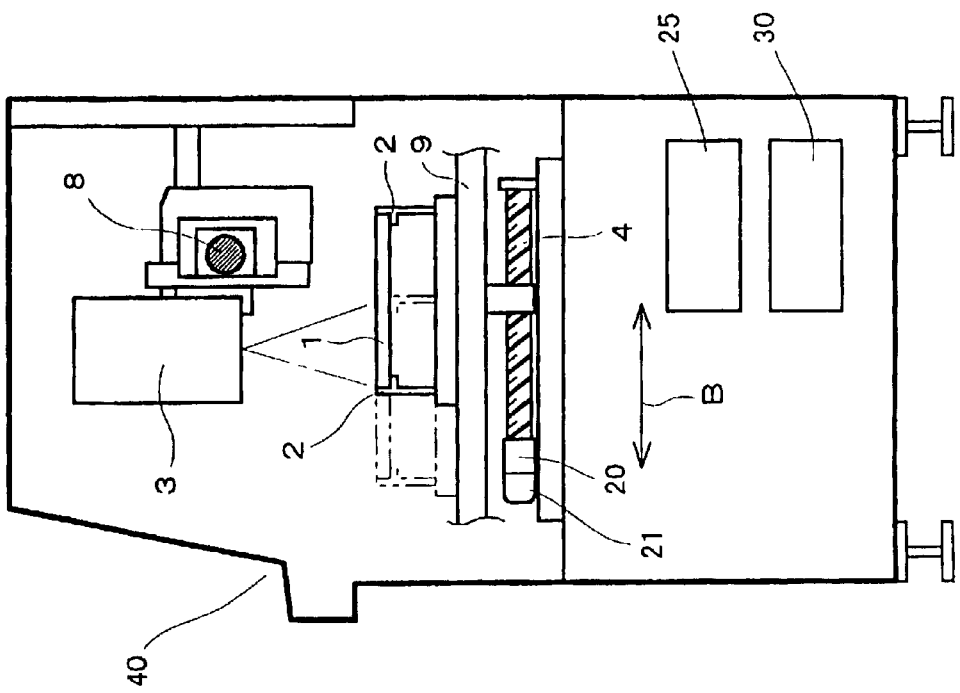

More specifically, as shown in FIGS. 2a and 2b, the inspection apparatus 40 is comprised of two movement shafts, namely the screw shaft 4 for moving the printed circuit board 1 which has been conveyed to an inspection position, along the breadth direction of the rails 2 (direction indicated by arrow B), and a movement shaft 8 for moving a line sensor camera 3 or a photography unit along the direction of conveyance of the board (direction indicated by arrow A).

Here, 9 represents a moving platform for mounting thereon the pair of rails 2, which is driven to move in the direction indicated by arrow B as the screw shaft 4 rotates; 20 a motor for rotationally driving the screw shaft 4; 21 a rotary encoder for detecting an amount of rotation of the motor 20; 22 a motor for rotationally driving the movement shaft 8; 23 a rotary encoder for detecting an amount of rotation of the motor 22; 25 a control unit for controlling the overall inspection apparatus including the motors 20 and 22; and 30 an image processing unit for processing image data photographed by the line sensor camera 3.

Figure 3:
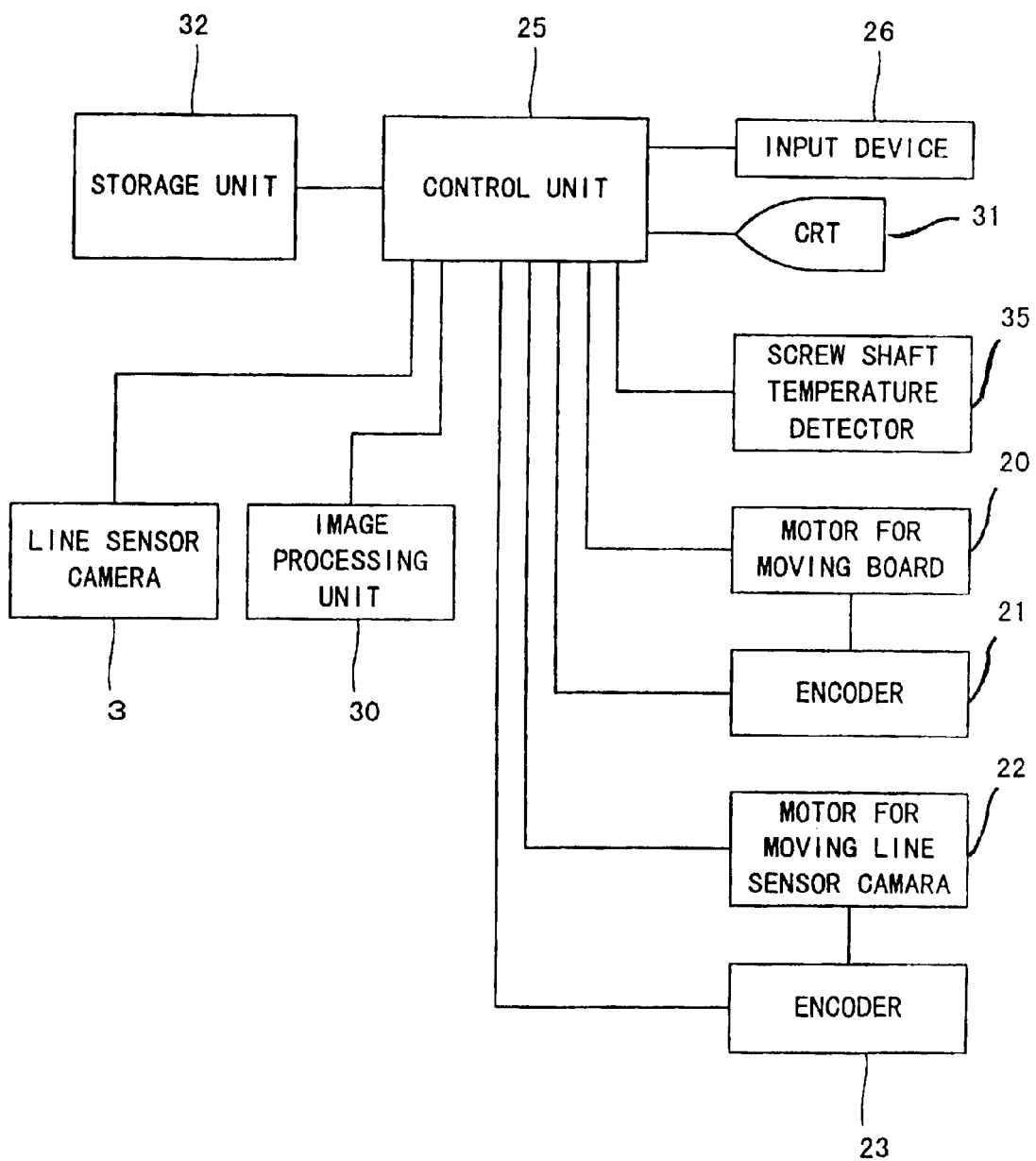
FIG. 3 is a block diagram of the inspection apparatus in the first embodiment of the present invention.

The control system of the inspection apparatus 40 is configured as shown in FIG. 3.

In FIG. 3, the control unit 25 is connected with an input device 26 and CRT 31, so that an operator operates the inspection apparatus 40 by inputting instructions, information data and so on to the input device 26 while watching the CRT 31. Represented by 32 is a storage unit for storing therein data input from the input device 26, control programs necessary to actuate the inspection apparatus 40, control parameters, image data photographed by the line sensor camera 3 and so on.

The control unit 25 rotationally drives the motor 20 for moving the board, and the amount of rotation of the motor 20 is detected by the encoder 21. Likewise, the control unit 25 rotationally drives the motor 22 for moving the line sensor camera, and the amount of rotation of the motor 22 is detected by the encoder 23.

The printed circuit board 1 is held by the pair of rails 2 constituting a pair of holding members, and first and second correction marks 6a and 6b for the holding members are provided on the side 51 of the rails 2 where the line sensor camera 3 starts reading.

The screw shaft 4 sometimes expands or contracts due to heat and other factors, with the passage of time, so that discrepancies can occur between coordinate positions where the first and second holding member correction marks 6a and 6b have been recognized on the rails 2 at a point of time t1, and coordinate positions where the first and second holding member correction marks 6a and 6b have been recognized on the rails 2 at another point of time t2 after a passage of a certain period of time from t1.

As a result, a positional discrepancy occurs at the first scan start position 5a and the second scan start position 5b, respectively, and a discrepancy occurs in the first and second inspection areas 7a and 7b.

Figure 4:
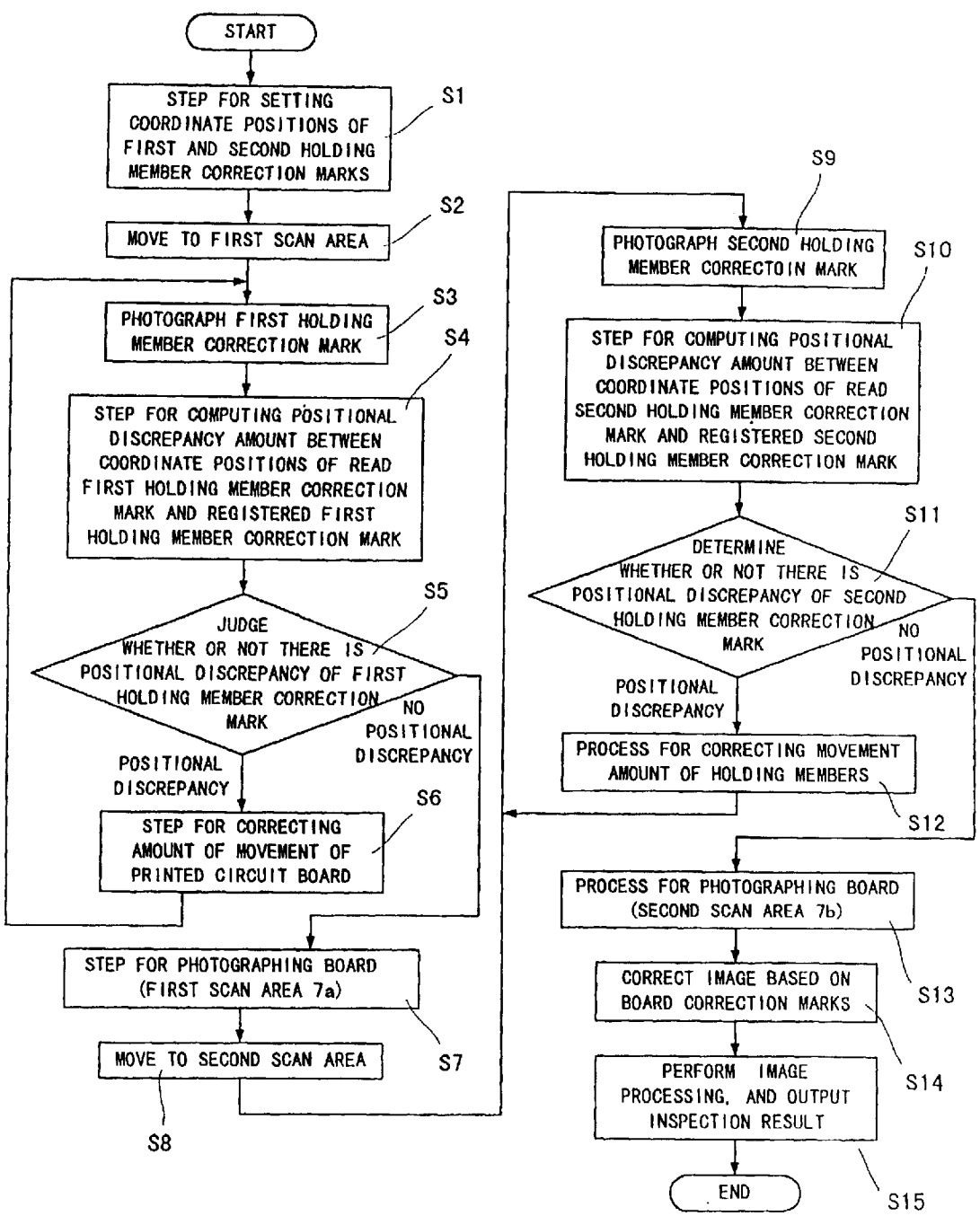
FIG. 4 is a flowchart showing an inspection method in the first embodiment of the present invention.

Thereupon, in this first embodiment, the coordinate positions of the first and second holding member correction marks 6a and 6b are read by the line sensor camera 3, and the control illustrated by the flow chart shown in FIG. 4 is performed by the control unit 25 so that the amount of movement of the printed circuit board 1 in the direction indicated by arrow B is corrected.

First, in step S1, the coordinate positions of the first and second correction marks 6a and 6b are set by the input device 26 and stored in the storage unit 32.

In step S2, the motor 20 is driven to move the printed circuit board 1 in the direction of B in order to photograph the first scan area of the printed circuit board 1.

In step S3, every time one printed circuit board 1 is inspected, or once every several boards have been inspected, or when a value measured by a screw shaft temperature detector 35 for detecting temperature of the screw shaft 4 exceeds a previously set threshold value, the first correction mark 6a provided on one of the rails 2 constituting the holding members is recognized, and in step S4, according to the instruction from the control unit 25, the line sensor camera 3 is moved in the direction A to photograph the first holding member correction mark 6a, and thus photographed correction mark is subjected to image processing by the image processing unit 30 so that the position of the first holding member correction mark 6a is detected. Then, the amount of positional discrepancy between the coordinate position of the first holding member correction mark 6a detected by photography and that of the set holding member correction mark 6a is computed.

When it is judged in step S5 that there is a discrepancy between the coordinate positions of the two kinds of the first correction marks 6a, the amount of movement of the printed circuit board 1 is corrected and the positional discrepancy of the first scan start position 5a is corrected in step S6.

Specifically, the amount of rotation of the motor 22 is detected by the encoder 23 in order that the motor 22 rotates for the same amount corresponding to the amount of positional discrepancy obtained in step S4, thereby correcting the amount of positional discrepancy and solving the problem associated with such discrepancy.

After the correction, the amount of coordinate positional discrepancy of the first holding member correction mark is detected again in steps S3 and S4, and in step S5, it is determined whether or not there exists the positional discrepancy. This is repeated until it is determined in step S5 that there exists no more positional discrepancy.

When it is judged in step S5 that there is no positional discrepancy, in step S7, the line sensor camera 3 is moved, for example, from a reading start side 51 toward a reading end side 52 as shown in FIG. 1, in order to photograph the first scan area 7a of the printed circuit board 1 by the line sensor camera 3.

At the same time, the first correction mark 6c provided on the printed circuit board 1 is photographed, and its center position is obtained by image processing by the image processing unit 30.

When it is judged in step S5 that there is no positional discrepancy, too, the printed circuit board 1 is photographed in step S7.

Next, in step S8, according to the instruction from the control unit 25, the motor 20 is rotationally driven for an amount of movement corresponding to the distance from the previously set first holding member correction mark 6a to the second holding member correction mark 6b, and the printed circuit board 1 is moved in the direction B to a position where the second scan area is photographed.

In step S9, according to the instruction from the control unit 25, the line sensor camera 3 is moved in the direction A, and the second holding member correction mark 6b is photographed. And in step S10, the amount of positional discrepancy between the coordinate position of the second holding member correction mark 6b which has been read and the coordinate position of the previously set second holding member correction mark 6b is computed.

When it is judged in step S11 that there is a coordinate positional discrepancy with the second holding member correction mark 6b, in the same manner as in step S6, the amount of movement of the printed circuit board 1 is corrected and the positional discrepancy of the first scan start position 5a is corrected. Such corrections are repeated in steps S9 and S10, until it is judged again that there is no positional discrepancy in step S11.

When it is judged that there is no positional discrepancy in step S11, the second scan area 7b of the printed circuit board 1 is photographed by the line sensor camera 3 in step S13. At the same time, the board correction mark 6d on the printed circuit board 1 is also photographed, and its center position is obtained through image processing by the image processing unit 30.

Next, in step S14, the amount of discrepancies between the recognized coordinate positions of the first and second board correction marks 6c and 6d obtained in step S7 and step S13, and the coordinate positions of the board correction marks 6c and 6d previously set is computed, and in order to solve the discrepancy amount, the image of the printed circuit board including the first scan area and the second scan area combined is corrected by employing the conventional method earlier mentioned so that the board correction marks 6c and 6d appearing on the image correspond to the previously set positions.

In step S15, the corrected image of the printed circuit board is subjected to image processing and inspection judgment, thereafter the result of inspection is output.

By performing such correction as described above, positional corrections can be performed to compensate for the expansion and contraction in movement shafts and in printed circuit boards caused by heat and other factors, even in inspection machines that are configured with biaxial movement shafts.

In the foregoing description, the first and second correction marks 6a and 6b are placed in an opposed relations to each other on the rails on the side where the line sensor camera 3 starts reading, but the present invention is not limited thereto or thereby, and their set positions can be adjusted as may be expedient.

Second Embodiment

Figure 5:
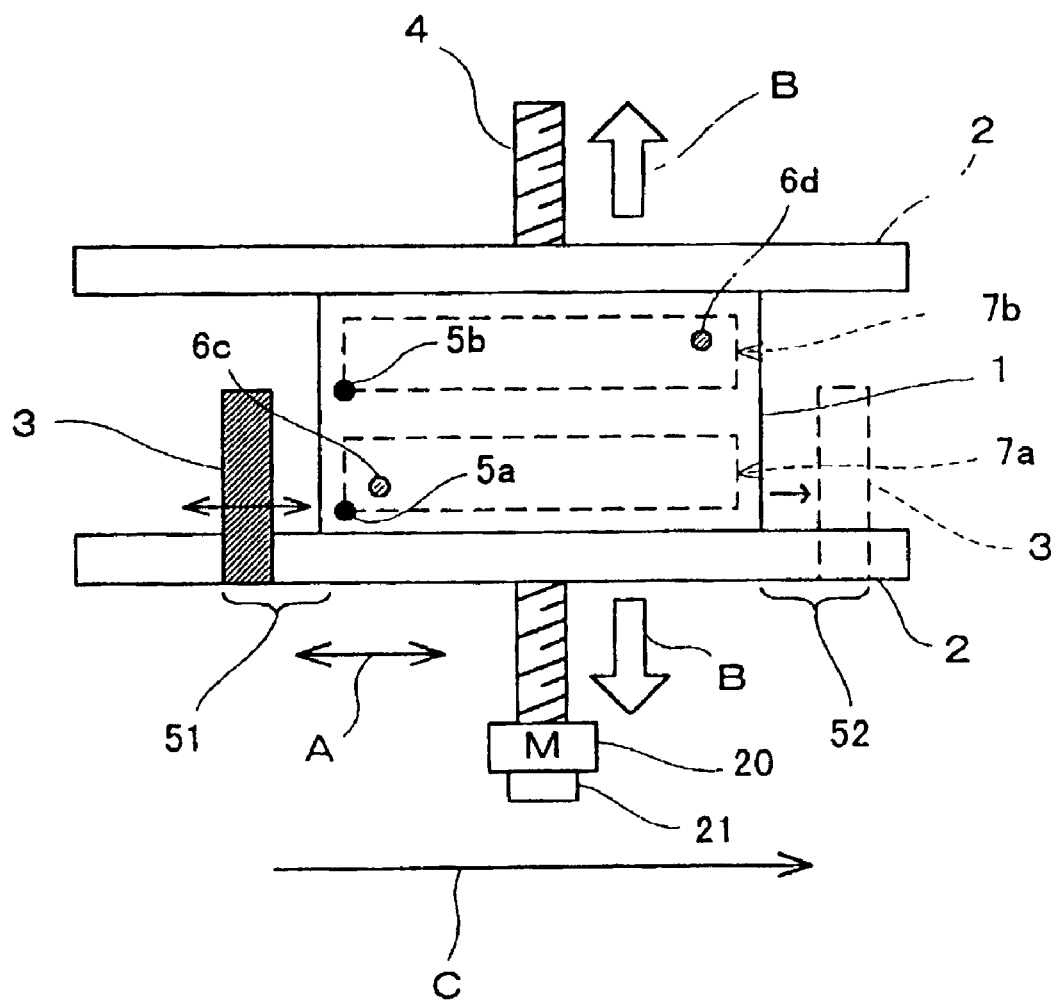
FIG. 5 is a schematic plan view of an inspection apparatus in a second embodiment of the present invention.
Figure 6:
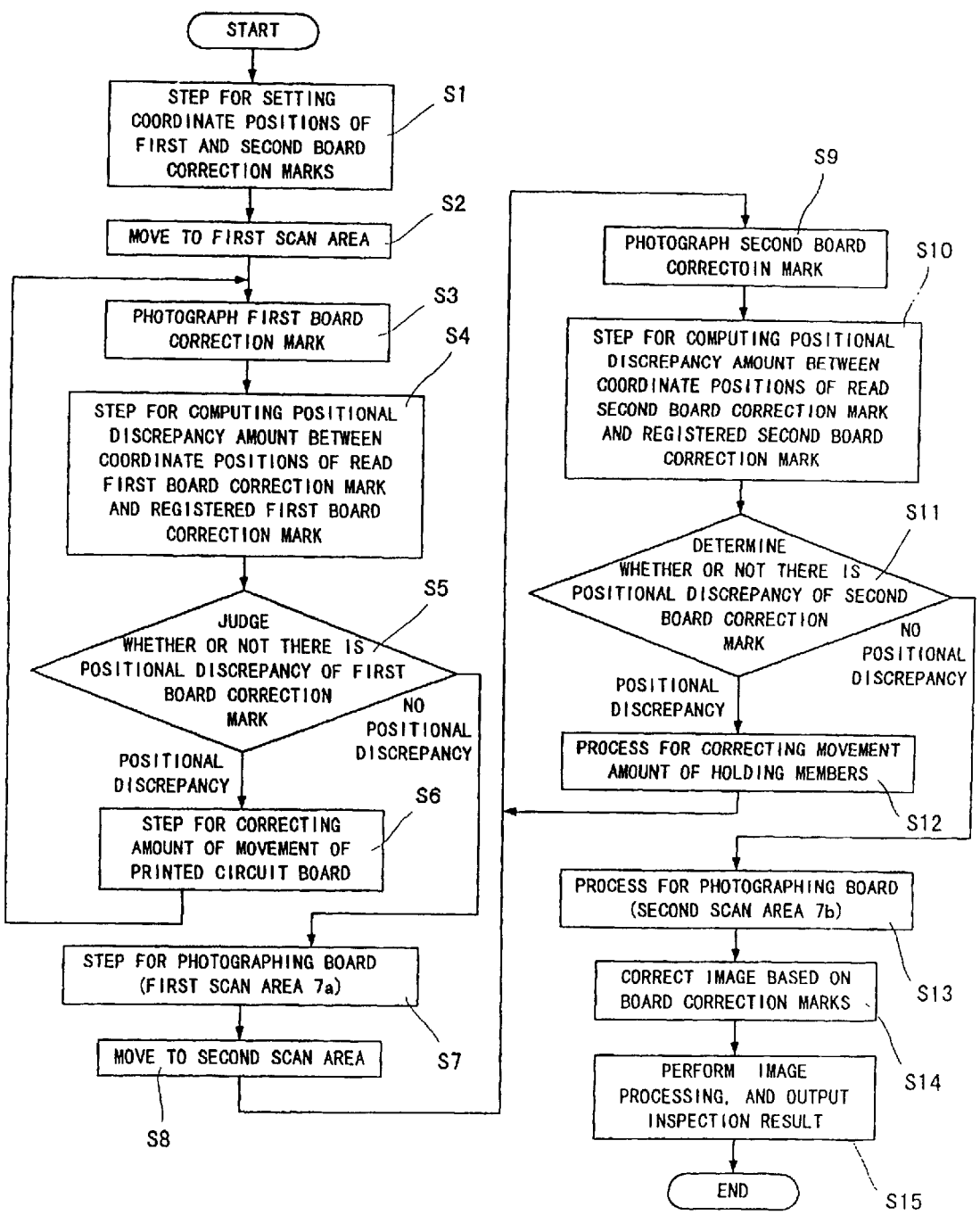
FIG. 6 is a flowchart showing an inspection method in the second embodiment of the present invention.
Figure 7:
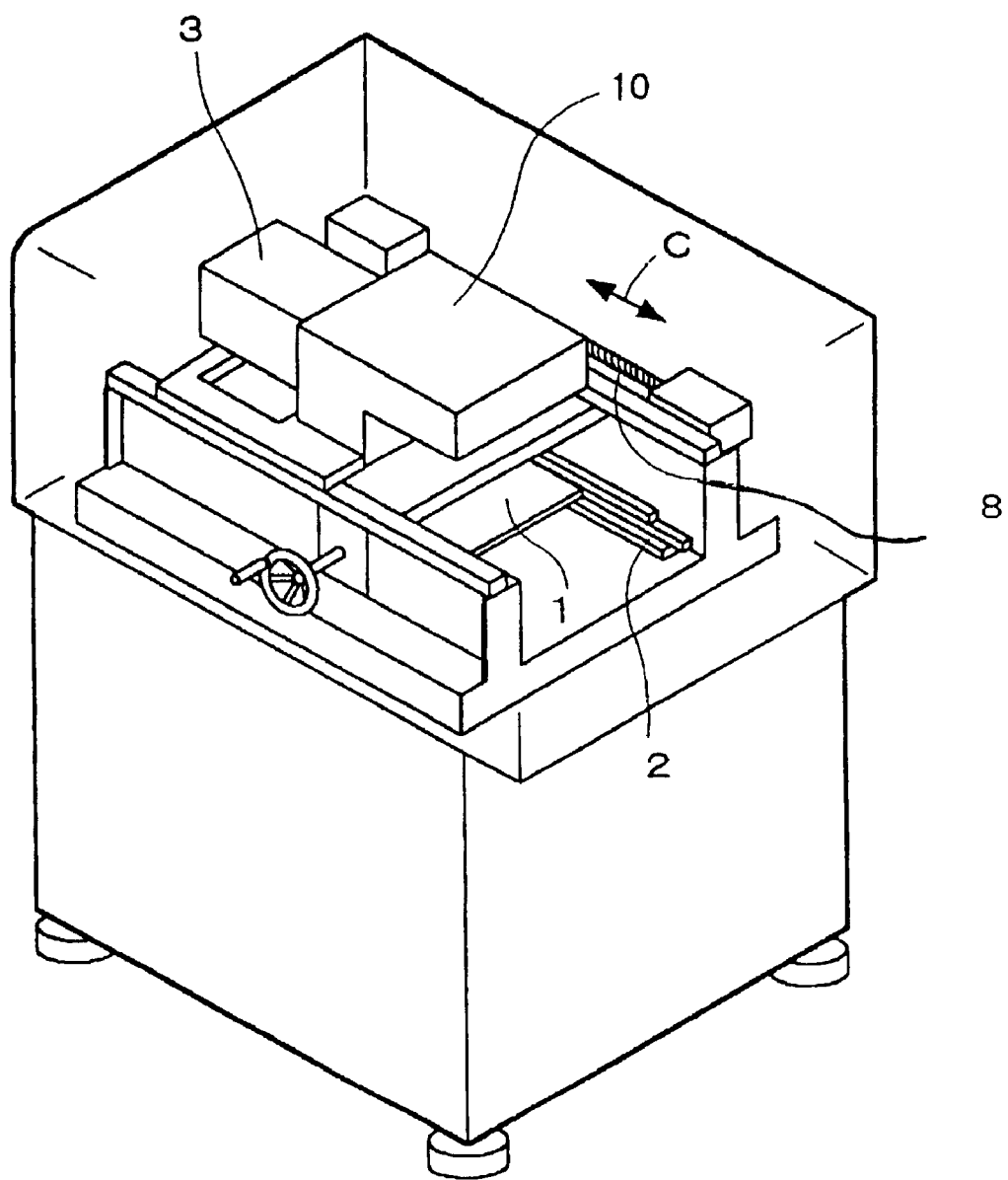
FIG. 7 is a perspective view of a conventional inspection apparatus.
Figure 8:
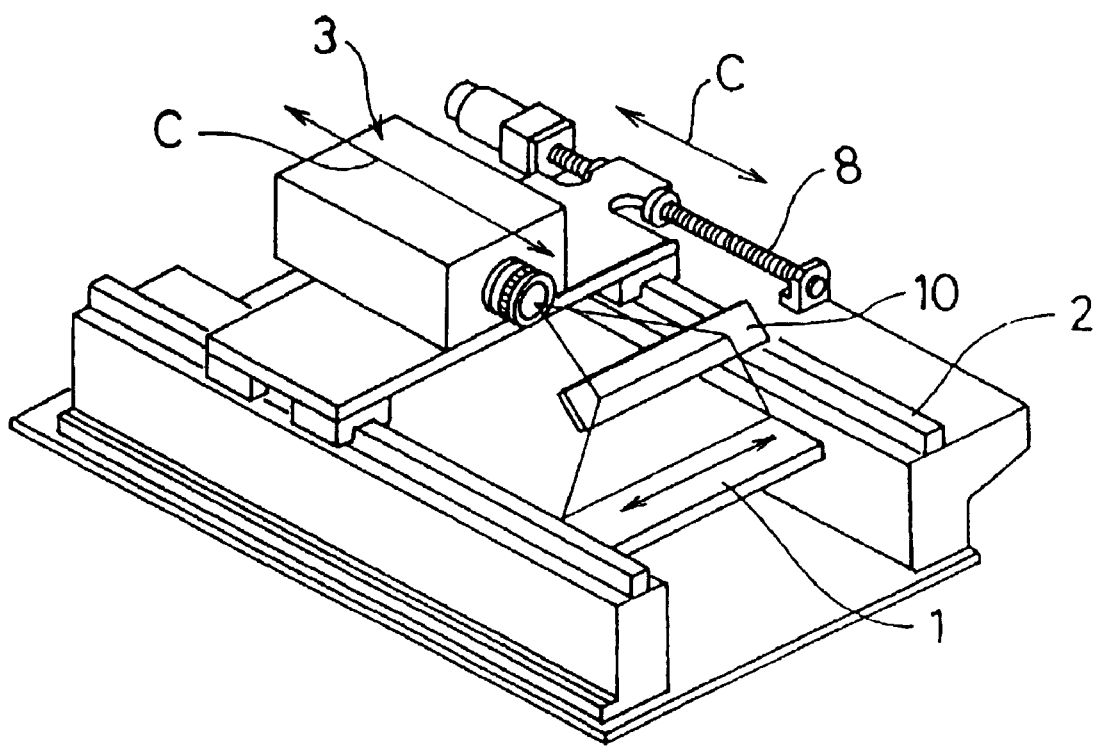
FIG. 8 is a perspective view of a main part of the conventional inspection apparatus.

Second embodiment of the present invention is shown in FIGS. 5 and 6.

In this embodiment, although there is a difference from the first embodiment described in the foregoing in that correction marks are provided on a printed circuit board 1, in other respects the basic configuration is the same as in the first embodiment.

Figure 9:
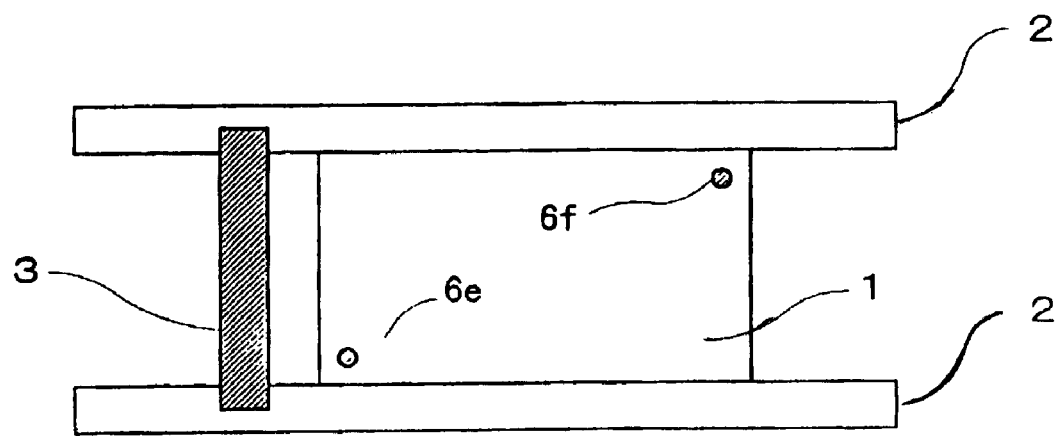
FIG. 9 is a schematic plan view of the conventional inspection apparatus.

Specifically, as shown in FIG. 5, a first board correction mark 6c is provided on a printed circuit board 1 on the side where a line sensor camera 3 starts reading the printed circuit board 1 as shown in FIG. 9 which shows a conventional example, and a second board correction mark 6d is provided on a diagonal line passing the first correction mark 6c.

The printed circuit board 1 conveyed to the inspection position is moved by a screw shaft 4 in the direction indicated by arrow B, and the line sensor camera 3 is moved in the direction indicated by arrow A, whereby a first scan area 7a and a second scan area 7b are subjected to inspection.

In an inspection apparatus configured in this way, when expansion or contraction occurs in the screw shaft 4 over the course of time due to heat and/or other factors, and a discrepancy occurs between the position obtained as a result of recognition of the board correction marks 6c and 6d on the printed circuit board 1 at some point of time and the position obtained as a result of recognition of the board correction marks 6c and 6d on the printed circuit board 1 after a passage of some period of time, the position of the printed circuit board 1 is corrected by the control unit shown in FIG. 6.

First, in step S1, the coordinate positions of the first and second board correction marks 6c and 6d are set by the input device 26 and stored in the storage unit 32.

In step S2, the motor 20 is driven to move the printed circuit board 1 in the direction of B in order to photograph the first scan area of the printed circuit board 1.

In step S3, every time one printed circuit board 1 is inspected, or once every several boards have been inspected, or when a value measured by a screw shaft temperature detector 35 for detecting temperature of the screw shaft 4 exceeds a previously set threshold value, the first board correction mark 6c provided on the printed circuit board is recognized, and in step S4, according to the instruction from the control unit 25, the line sensor camera 3 is moved in the direction A to photograph the first board correction mark 6c, and thus photographed correction mark is subjected to image processing by the image processing unit 30 so that the position of the first board correction mark 6c is detected. Then, the amount of positional discrepancy between the coordinate position of the first board correction mark 6c detected by photography and that of the set board correction mark 6c is computed.

When it is judged in step S5 that there is a discrepancy between the coordinate positions of the two kinds of the first board correction marks 6c, the amount of movement of the printed circuit board 1 is corrected and the positional discrepancy of the first scan start position 5a is corrected in step S6.

Specifically, the amount of rotation of the motor 22 is detected by the encoder 23 in order that the motor 22 rotates for the same amount corresponding to the amount of positional discrepancy obtained in step S4, thereby correcting the amount of positional discrepancy and solving the problem associated with such discrepancy.

After the correction, the amount of coordinate positional discrepancy of the first board correction mark is detected again in steps S3 and S4, and in step S5, it is determined whether or not there exists the positional discrepancy. This is repeated until it is determined in step S5 that there exists no more positional discrepancy.

When it is judged in step S5 that there is no positional discrepancy, in step S7, the line sensor camera 3 is moved, for example, from a reading start side 51 toward a reading end side 52 as shown in FIG. 5, in order to photograph the first scan area 7a of the printed circuit board 1 by the line sensor camera 3.

At the same time, the first board correction mark 6c provided on the printed circuit board 1 is photographed, and its center position is obtained by image processing by the image processing unit 30.

When it is judged in step S5 that there is no positional discrepancy, too, the printed circuit board 1 is photographed in step S7.

Next, in step S8, according to the instruction from the control unit 25, the motor 20 is rotationally driven for an amount of movement in the direction B corresponding to the distance from the previously set first board correction mark 6c to the second board correction mark 6d, and the printed circuit board 1 is moved in the direction B to a position where the second scan area is photographed.

In step S9, according to the instruction from the control unit 25, the line sensor camera 3 is moved in the direction A, and the second board correction mark 6d is photographed. And in step S10, the amount of positional discrepancy between the coordinate position of the second board correction mark 6d which has been read and the coordinate position of the previously set second board correction mark 6d is computed.

When it is judged in step S11 that there is a coordinate positional discrepancy with the second board correction mark 6d, in the same manner as in step S6, the amount of movement of the printed circuit board 1 is corrected and the positional discrepancy of the first scan start position 5a is corrected. Such corrections are repeated in steps S9 and S10, until it is judged again that there is no positional discrepancy in step S11.

When it is judged that there is no positional discrepancy in step S11, the second scan area 7b of the printed circuit board 1 is photographed by the line sensor camera 3 in step S13. At the same time, the board correction mark 6d on the printed circuit board 1 is also photographed, and its center position is obtained through image processing by the image processing unit 30.

Next, in step S14, the amount of discrepancies between the recognized coordinate positions of the first and second board correction marks 6c and 6d obtained in step S7 and step S13, and the coordinate positions of the board correction marks 6c and 6d previously set is computed, and in order to solve the discrepancy amount, the image of the printed circuit board including the first scan area and the second scan area combined is corrected by employing the conventional method earlier mentioned so that the board correction marks 6c and 6d appearing on the image correspond to the previously set positions.

In step S15, the corrected image of the printed circuit board is subjected to image processing and inspection judgment, thereafter the result of inspection is output.

By performing such correction as described above, positional corrections can be performed to compensate for the expansion and contraction in movement shafts and in printed circuit boards due to heat and/or other factors, even in inspection machines that are configured with two movement shafts as in the first embodiment described earlier.

In the foregoing description, the positional discrepancy of the screw shaft is corrected using the same first and second correction marks as used in the conventional expansion and contraction correction method, but the present invention is not limited thereto or thereby, nor is there any particular limitation on the positions of the first and second board correction marks used in the correction shown in FIG. 5.

In the embodiments mentioned above, description has been made by citing a ball screw as an element constituting the movement shaft, but the present invention is not limited thereto or thereby, and can be embodied with some other drive means such as a timing belt or the like.

As is clear from the embodiments mentioned above, according to the inspection method of the present invention, the coordinate positions of correction marks applied to holding members are read by a line sensor camera, an amount of positional discrepancy of a board is computed by comparing previously set coordinate positions of the correction marks with coordinate positions of the read correction marks, and when there are discrepancies between the two kinds of coordinate positions, photographing noted earlier is performed after correcting an amount of movement of the holding members based on the amount of positional discrepancy of the board, whereby it is possible to inspect a large-size board by laterally moving the board and photographing the same for a plural number of times before and after the lateral moving, and it is also possible to achieve high-precision inspection.

Further, with the inspection apparatus of the present invention, the inspection method of the present invention can be easily implemented by providing a control unit configured so that the coordinate positions of the correction marks applied to the holding members are read by the line sensor camera, an amount of positional discrepancy of the board is computed by comparing the coordinate positions of the previously set correction marks with the coordinate positions of the read correction marks, and when there are coordinate-positional discrepancies between the two kind of correction marks, the photographing is performed after correcting the amount of movement of the holding members based on the amount of positional discrepancy of the board.

What is claimed is:

1. An inspection method for inspecting a to-be-inspected board by photographing the board that has been conveyed to an inspection position, in which a pair of holding members for holding the board are moved to move the board in a direction crossing a scanning direction of a photography unit and the board that has been positioned is scanned by the photography unit along the direction of said conveyance of the board, the inspection method comprising:

reading coordinate positions of board correction marks applied to said board by said photography unit;

computing an amount of positional discrepancy of said board by comparing coordinate positions of board correction marks previously set with the coordinate positions of the board correction marks having been read; and when there are discrepancies between said two kinds of coordinate positions, carrying out said photographing after correcting an amount of movement of the holding members based on said amount of positional discrepancy of the board.

2. The inspection method according to claim 1, wherein a first board correction mark and a second board correction mark are provided on the board, said first board correction mark being provided on the side where the photography unit starts reading, said second board correction mark being provided on a diagonal line passing said first board correction mark.

3. An inspection apparatus for inspecting a to-be-inspected board by photographing the board that has been conveyed to an inspection position, in which a pair of holding members constituted of a pair of rails for holding the board are moved to move the board in a direction crossing a scanning direction of a photography unit and the board that has been positioned is scanned by the photography unit along the direction of said conveyance of the board, the inspection apparatus comprising:

a control unit configured to read coordinate positions of board correction marks applied to said board by the photography unit, to compute an amount of positional discrepancy of the board by comparing coordinate positions of board correction marks previously set with the coordinate positions of the board correction marks having been read, and when there are discrepancies between said two kinds of coordinate positions, to carry out the photographing after correcting an amount of movement of the holding members based on said amount of positional discrepancy of the board.

* * * * *